Figure 1:
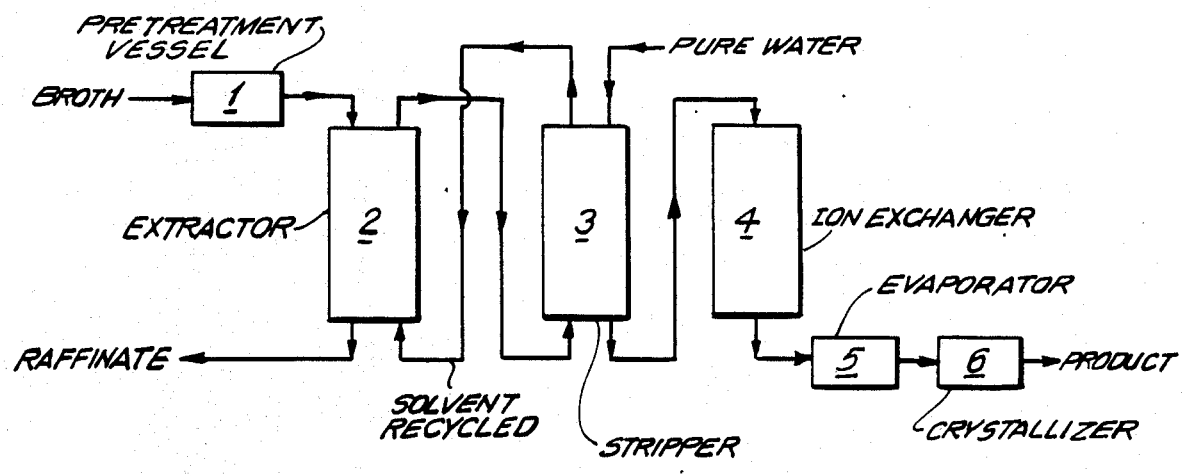

United States Patent [19]

Su et al.

[11] Patent Number: 4,705,894

[45] Date of Patent: Nov. 10, 1987

[54] PROCESS FOR RECOVERY OF ORGANIC ACIDS FROM AQUEOUS SOLUTIONS

[76] Inventors: Yuanfu Su; Yuming Jiang, both of 22 Fl., Wu Sang House, 655 Nathan Road, Kowloon, Hong Kong

[21] Appl. No.: 842,489

[22] Filed: Mar. 21, 1986

Related U.S. Application Data

[63] Continuation-in-part of Ser. No. 584,899, Feb. 29, 1984.

[51] Int. Cl.$^4$ .............................................. C07C 59/265
[52] U.S. Cl. ................................. 562/580; 562/593; 562/582; 562/584; 562/585; 562/597
[58] Field of Search ............... 562/580, 593, 582, 584, 562/585, 597

[56] References Cited

U.S. PATENT DOCUMENTS 3,816,524  6/1974  Grinstead ............................ 562/593
4,365,094  12/1982  Boileau et al. ......................... 568/14

Primary Examiner—Paul J. Killos
Assistant Examiner—Bruce D. Gray
Attorney, Agent, or Firm—Morgan & Finnegan

[57] ABSTRACT

A mixture of trialkyl phosphine oxides (HTRPO) was prepared having the formula:

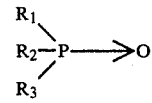

wherein $R_1$, $R_2$ and $R_3$ are same or different alkyl groups of 5 to 9 carbon atoms and the total number of carbon atoms and the total number of carbon atoms per molecule is from 15 to 27. The mixture of trialkyl phosphine oxides (HTRPO) is useful as an extractant for recovering acids from aqueous solutions.

4 Claims, 1 Drawing Figure

PROCESS FOR RECOVERY OF ORGANIC ACIDS FROM AQUEOUS SOLUTIONS

CROSS REFERENCE TO RELATED APPLICATIONS

This is a continuation-in-part of application Ser. No. 584,899 filed Feb. 29, 1984.

BACKGROUND OF THE INVENTION

This invention relates to a mixture of trialkyl phosphine oxides as an extractant for the recovery of organic acids from aqueous solutions.

Recovery of acid from aqueous solution is extensively practiced in industry. Organic acids, such as citric acid, malic acid, tartaric acid and oxalic acid, have been commercially produced by fermentation or by chemical synthesis. Because of impurities existing in fermentation broths, the acid is precipitated as a calcium salt and is liberated by adding sulfuric acid so as to obtain pure organic acid solution. Then, the final product of the acid is obtained after evaporation and crystallization. This procedure has the disadvantages of requiring expendable lime and sulfuric acid as well as disposal of calcium sulfate.

A liquid-liquid extraction process by means of different extractants and techniques, known as an alternative means of recovery of organic acid from aqueous solution, has also been proposed in the prior art.

Procedures which employ amines are disclosed in British Pat. No. 1,428,018 and U.S. Pat. No. 2,539,472. U.S. Pat. No. 3,944,606 disclosed the use of amines to produce citrate. Because of the lower selectivity of amines, the symbiosis acid, such as oxalic acid, from fermentation would be co-extracted into solvent of amine during the process of extraction, and the unknown toxicity of amines limits their use for edible purposes.

The phosphoryl-containing extractant is also used by the invention of U.S. Pat. No. 3,816,524 and Japan Pat. No. 47-5715. However, expensive centrifugal equipment has to be used in treating the emulsion existing in the extraction of fermentation broth.

U.S. Pat. No. 4,571,671 discloses the use of amides to extract citric acid and European Pat. No. 0,049,426 discloses a mixture of amines and water immiscible organic acid as solvent.

The present invention develops a process for the recovery of organic acid from aqueous solution by extraction. The fermentaton broth containing the organic acid is pretreated by active carbon in order to prevent emulsion, then the pretreated aqueous solution is extracted without emulsion in any equipment, such as a Mixture-settler and several columns. The extractants are phosphoryl-containing compounds, wherein a mixture of trialkyl phosphine oxides (HTRPO) which is not disclosed by any prior art is more suitable, because of its better extraction ability and selectivity as well as good adaptability for various processes in the extraction and stripping.

Furthermore, none of the prior art suggests the process in which the citric acid for edible and pharmaceutical purposes is recovered from fermentation broth by extraction.

SUMMARY OF THE INVENTION

In accordance with the present invention, a process of recovery of organic acids from aqueous solutions or fermentation broths thereof is provided which comprises pretreating the broth by means of granular active carbon prior to extraction, and extracting the pretreated solutions of the acid with a water immiscible solvent mixture of a phosphoryl-containing extractant and a suitable water immiscible diluent. The acid is selected from the class consisting of citric acid, malic acid, oxalic acid and tartaric acid.

The method for preparing a mixture of trialkyl phosphine oxides (HTRPO) is also provided in the invention, which is preferential among the phosphoryl-containing extractants.

DESCRIPTION OF THE INVENTION

The aqueous solution used as starting material in the present invention includes fermentation broth containing citric acid, malic acid, tartaric acid or oxalic acid. The concentration of said acid in the broth is from 2 to 30 percent by weight.

It is found in the present invention that protein and other unknown substances existing in fermentation broth are the main cause of a stable emulsion which prevents the operation of extraction with fermentation broth. It is also disclosed that the removal of protein and other unknown substances can be carried out by means of adsorbing on active carbon or other chemical means.

The adsorption formula is as follows:

$$X/M = KC^{0.592}$$

Where
X = amount absorbed
M = amount of carbon used
C = amount absorbed at equilibrium
K = experimental constant The particle size of active carbon used in the invention is from 20 to 100 mesh, and preferably from 40 to 60 mesh. The specific surface of granular active carbon is from 1500 to 3000 $M^2/g$, and preferably from 2000 to 25000 $M^2/g$. The porosity diameter of granular active carbon is from 5 to 20A, and preferably from 10 to 15A. The adsorption process is carried out in a column or fluidized bed packed with said granular active carbon before extraction of the aqueous solution. The temperature of the adsorption bed is different from common absorption processes wherein the temperature should be held as low as possible. Whereas, the temperature range of the process of the present invent is maintained at from about 40° to 80° C. and preferably from 50° to 70° C. The flow rate of broth is from 1 to 10 $M^3/M^2$ hr and preferably from 2 to 5 $M^3/M^2$ hr.

When the pretreated aqueous solution is contacted with the water immiscible solvent mixture containing the extractant proposed in the present invention, no emulsion exists in the interface between the solvent mixture and aqueous solution.

The phosphoryl-containing extractants disclosed in the present invention are selected from the group consisting of:

(a) Trialkyl phosphine oxides,

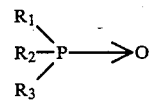

wherein $R_1$, $R_2$, and $R_3$ are the same or different alkyl groups of 2 to 10 carbon atoms.

A mixture of trialkyl phosphine oxides (HTRPO) is preferred, in which the total number of carbon atoms per molecule is from 15 to 27, and $R_1$, $R_2$, and $R_3$ are the same or different alkyl groups of 5 to 9 carbon atoms.

(b) Trialkyl phosphates,

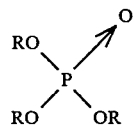

Wherein each R is alkyl group of 2 to 8 carbon atoms, such as tributyl phosphate (TBP).

(c) Dialkyl alkyl phosphonates,

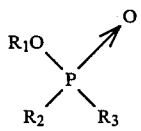

Wherein $R_1$, $R_2$, and $R_3$ are the same or different alkyl groups of 2 to 8 carbon atoms.

The diluents proposed in the present invention comprise aliphatic hydrocarbons, aromatic hydrocarbons, kerosine, sulfonated kerosine or ethers. The proportion by volume of extractant: Diluent is from 5:1 to 1:4.

In the present invention the loaded water immiscible solvent mixture is stripped with pure water or an aqueous solution of alkali. The temperature of stripping with pure water is from 50° to 90° C., and preferably ffrom 80° to 90° C.

The method for preparation of the mixture of trialkyl phosphine oxides (HTRPO) is also disclosed in the present invention, which comprises reacting a mixture of monohydric alcohol of 5 to 9 carbon atoms having the boiling point of 160° to 190° C. with iodine, and reacting the resultant product with red phosphours and nitric acid, then collecting the fraction at 160° to 260° C. under a vacuum pressure of 640 to 650 mm Hg as the mixture of trialkyl phosphine oxides (HTRPO).

A second method involves the oxidation of trialkyl phosphine according to the following reaction:

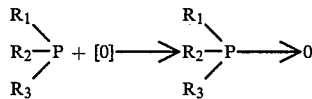

wherein $(R_1R_2R_3)P$ is produced by the reaction of alkene and phosphine, $PH_3$.

A third method involves the use of a Grignard reagent. A mixture of monohydroxy alcohols with 5 to 9 carbon atoms is reacted with chlorine sulfoxide in the presence of DMF to form alkyl chlorides. Magnesuim powder is added to the reaction mixture in the presence of ether. The Grignard reagent so formed is reacted with phosphorus oxytrichloride, $POCl_3$. The resulting mixture of trialkyl phosphine oxides is then purified by vacuum distillation.

The key step in the third method is that the reaction involving the Grignard reagent must be completely free of alcohol and water, otherwise an intense explosion may result. The problem can be solved by using absorption techniques.

The process proposed by the present invention is especially useful for the extraction of the fermentation broth containing citric acid from the fermentation of dried sweet potato, molasses and starch to produce citric acid for edible and pharmaceutical purposes as well as trisodium citrate. The invention is described in further detail in the following examples.

EXAMPLE 1

The mixture of monohydric alcohols of 5 to 9 carbon atoms was distilled under atmospheric pressure. The collected fraction of 160° to 180° C. was reacted with iodine at a temperature from 100° to 130° C. The resulting alkyl iodide was reacted with red phosphorus by adding nitric acid, then the fraction of 160° to 260° C. under vacuum pressure of 640-650 mm Hg was collected as a mixture of trialkyl phosphine oxides (HTRPO). The data of infra-red spectra analysis, element analysis and average molecular weights showed that the product was a mixture of trialkyl phosphine oxides containing 15 to 27 carbon atoms.

EXAMPLE 2

A mixture of alkene gas was reacted with phosphine, $PH_3$. Nitric acid was added to the mixture under gentle stirring in a vessel under vacuum pressure. The products were collected at a vacuum pressure of 640-650 mm Hg. A mixture of trialkyl phosphine oxides (HTRPO) was produced. The results of infrared analysis, elemental analysis and average molecular weights showed that the product was a mixture.

EXAMPLE 3

A mixture of monohydric alcohols of 5 to 9 carbon atoms awas distilled under atmospheric pressure. The fraction collected at 160° C.-180° C. was reacted with chlorine sulfoxide in the presence of DMF at a stoichiometric ratio of 1:1 to form alkyl chorides.

Magnesium powder was added to the reactor in the presence of ether. The Grignard reagent so formed was reacted with phosphorus oxytrichloride. The product was collected at a vacuum pressure of 640-650 mm Hg as a mixture of trialkyl phosphine oxides (HTRPO). The results of infrared analysis, elemental analysis and average molecular weights showed that the product was a mixture of trialkyl phosphine oxides containing 15 to 27 carbon atoms.

EXAMPLE 4

Extraction of aqueous solution containing 9.0% by weight citric acid was carried out in a separating funnel at 30° C. by the extractant HTRPO described in example 1. The diluent was hexane, phase ratio (O/A) was 1, and contacting time was 2 minutes. The distribution coefficients of different proportion between the extractant and the diluent are shown as Table 1.

TABLE 1

| proportion (vol %) | | distribution |
|---|---|---|
| HTRPO | Hexane | coefficient |
| 20 | 80 | 0.352 |
| 40 | 60 | 1.52 |
| 60 | 40 | 2.71 |

EXAMPLE 5

Crude broth from fermentation of dried sweet potato containing 116 g/l citric acid and 0.40% protein by weight was introduced into a column 50 mm in diameter packed with granular active carbon at 65° C. The flow rate of the broth was 50 ml/min.

Table 2 below shows that the physical and chemical properties of the fermentation broth were slightly changed after pretreatment, and that some of the proteinaceous and unknown substances were removed. This shows that the pretreatment is not a separation process, but is useful only to prevent emulsion.

TABLE 2

|  | Before Treatment | After Treatment |
| --- | --- | --- |
| Citric acid, g/l | 87.5 | 91.2 |
| density | 1.045 | 1.040 |
| protein % by weight | 0.3969 | 0.1810 |
| dioptre index | 1.4374 | 1.4365 |
| viscosity, CP | 1.466 | 1.433 |
| surface tension, dyne/cm. | 8.95 | 12.32 |

The adsorbed solution containing 110 g/l citric acid and 0.17% protein by weight was then contacted with a solvent mixture of the extractant and the diluent described above in a mixture-settler and a rotating disc contactor (RDC), in which no emulsion occured in the interface between the solvent mixture and the aqueous solution.

EXAMPLE 6

According to the flow sheet shown as FIG. 1 of the accompanying drawing, the fermentation broth described in Example 5 was introduced into pretreatment vessel (1). The obtained aqueous solution was extracted by a solvent which was composed of 40% by volume of HTRPO and 65% volume of sulfonated kerosine in extractor (2) at ambient temperature, and the flow rates of the aqueous solution and the solvent were 5 l/hr and 12.5 l/hr respectively. The loaded solvent mixture was then stripped with pure water in stripper (3) at 80° C. and with a water flow rate of 4 l/hr. The aqueous phase containing 150 g/l of citric acid from stripper (3) passed through ion-exchanger (4), evaporator (5) and crystallizer (6) in turn, and the final product was monohydrate citric acid.

The solvent from stripper (3) was recycled into extractor (2). Both extractor (2) and stripper (3) used here were mixture-settlers.

EXAMPLE 7

According to the flow sheet shown as FIG. 1, the fermentation broth described in Example 5 was introduced into pretreatment vessel (1), the obtained aqueous solution was extracted by solvent composed of 70% TBP by volume and 30% sulfonated kerosine by volume in extractor (2) at 10° C., and the loaded organic phase was stripped with pure water in stripper (3) at 60° C. The aqueous phase containing 120 g/l citric acid from stripper (3) entered into ion exchange (4), evaporator (5) and crystallizer (6) in turn, and the final product was monohydrate citric acid.

Both extractor (2) and stripper (3) used here were RDC (Rotating Disc Contactor).

EXAMPLE 8

Citric acid produced from Example 6 and Example 7 satisfied the requirements of the British Pharmaceutical Codex (1980); the data of chemical analysis are shown as Table 3.

Also no organic phosphorus residues were left in the crystals of citric acid.

TABLE 3

| Exam. Item | Demands of B.P. | Products from Ex. (6) | Products from Ex. (7) |
| --- | --- | --- | --- |
| Identification | Yes | Yes | Yes |
| Citric acid | 99% | 99.4% | 99.5% |
| Oxalic salt | clear | clear | clear |
| Sulphate % | <0.05 | 0.005 | 0.003 |
| Calcium salt | no white precipitation | no | no |
| As ppm | <2 | 0.25 | 0.25 |
| Fe ppm | <50 | 1 | 3 |
| Pb ppm | <5 | 1 | 1 |
| Ashes % | <0.10 | 0.025 | 0.031 |
| Carbonizables (O.D) | <0.90 | 0.32 | 0.37 |

Based on the data shown as Table 3 as well as the solubility and toxicity of extractant etc, the HTRPO is considered as the best extractant among the extractants.

EXAMPLE 9

Exraction of pretreated aqueous solution containing 100 g/l oxalic acid was carried out in a separating funnel at 30° C. and the phase ratio (O/A) was 1. The extractant and diluent were diheptyl ethyl phosphonate and sulfonated kerosine, respectively. The data of distribution coefficients of different proportions between the extractant and the diluent are shown in Table 4.

TABLE 4

| Proportion (Vol. %) | | Distribution coefficient |
| --- | --- | --- |
| Diheptyl ethyl phosphonate | Sulfonated kerosine | |
| 100 | 0 | 2.09 |
| 80 | 20 | 1.42 |
| 65 | 35 | 1.02 |
| 50 | 50 | 0.76 |
| 30 | 70 | 0.33 |

EXAMPLE 10

Extraction of 100 ml aqueous solution containing 100 g/l tartaric acid was carried out in a separating funnel, the phase ratio (O/A) was 1, the contacting time was 5 minutes, and the solvent was composed of 80% HTRPO by volume and 20% dibutyl ether by volume. The data of distribution coefficients at different temperatures are shown as Table 5. The solution had been pretreated before the extraction.

TABLE 5

| Temperature °C. | 16 | 30 | 50 | 65 | 80 |
| --- | --- | --- | --- | --- | --- |
| distribution coefficient | 3.07 | 2.77 | 1.81 | 1.80 | 1.20 |

EXAMPLE 11

Extraction of pretreated aqueous solution containing 100 g/l malic acid was carried out in a separating funnel at 30° C., the phase ratio (O/A) was 1, and the extractant and diluent were HTRPO and hexane respectively. The data of distribution coefficient of different proportion between the extractant and the diluent are shown as Table 6.

TABLE 6

| Proportion (Vol %) | | distribution |
|---|---|---|
| HTRPO | Hexane | coefficient |
| 100 | 0 | 2.35 |
| 80 | 20 | 1.46 |
| 65 | 35 | 1.07 |
| 50 | 50 | 0.53 |
| 30 | 70 | 0.46 |

EXAMPLE 12

According to the flow sheet shown as FIG. 1, the fermentation broth described in Example 5 was introduced into pretreatment (1) and extractor (2) in which the solvent mixture was described in Example 4. Then 200 ml of loaded organic phase containing 37.8 g/l citric acid was back-extracted with 47.3 g of 10% sodium hydroxide aqueous solution and all the citric acid was thus converted into tri-sodium citrate. 9 g of $Na_3C_6H_5O_7 \cdot 5H_2O$ in a high purity was obtained after evaporation and crystallization.

What is claimed is:

1. A process for the recovery of a carboxylic acid selected from the group consisting of citric acid, malic acid, tartaric acid and oxalic acid from fermentation broths wherein the concentrations of the carboxylic acid is from about 2 to about 30 percent by weight, comprising the steps:

(a) Pretreating the fermentation broth at a temperature in the range of about 40° C. and 80° C. with granular active carbon with a particle size in the range between 20 to 100 mesh, and a specific surface area of from 1500 to 3000 $M^2/g$ and a porosity of from about 5A to 20A;

(b) Extracting the pretreated broth at a temperature in the range of about 10° C. to about 35° C. with an extractant in a water immiscible solvent selected from the group consisting of aliphatic hydrocarbons, aromatic hydrocarbons, kerosine, sulfonated kerosine and ethers, the extractant being

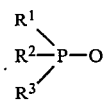

a mixture of trialkyl phosphine oxides having a total of 15 to 27 carbon atoms and wherein $R^1$, $R^2$ and $R^3$ are the same or different alkyl groups of 5 to 9 carbon atoms; and (c) re-extracting the extract with distilled water at a temperature in the range of from about 5° C. to about 90° C.

2. A process according to claim 1 wherein the carboxylic acid is citric acid and wherein the water immiscible solvent is sulfonated kerosine.

3. A process according to claim 1 wherein the temperature for pretreating the fermentation broth with granular active carbon is in the range of about 50° C. to 70° C.

4. A process according to claim 2 wherein the temperature for pretreating the fermentation broth with granular active carbon is in the range of about 50° C. to 70° C.

* * * * *